United States Patent [19]

Staats

[11] Patent Number: 5,336,305
[45] Date of Patent: Aug. 9, 1994

[54] FLEXIBLE MATERIAL HAVING BARRIER PROPERTIES

[75] Inventor: Victor Staats, Miami Beach, Fla.

[73] Assignee: International Laboratory Technology Corp., Miami, Fla.

[21] Appl. No.: 86,022

[22] Filed: Jul. 6, 1993

[51] Int. Cl.⁵ .............................................. C09D 5/14
[52] U.S. Cl. .............................. 106/18.32; 106/18.35; 424/404; 424/405; 424/406; 514/642; 514/643; 523/122
[58] Field of Search ............... 106/18.32, 18.35, 15.05; 424/405, 406, 404; 514/642, 643; 523/122

[56] References Cited

U.S. PATENT DOCUMENTS

| | | | |
|---|---|---|---|
| 4,379,890 | 4/1983 | Konietzny et al. | 106/18.32 |
| 4,554,185 | 11/1985 | Lane et al. | 106/18.32 |
| 4,576,838 | 3/1986 | Rosen et al. | 106/18.32 |
| 4,596,724 | 6/1986 | Lane et al. | 106/18.32 |
| 4,764,214 | 8/1988 | Marx et al. | 106/18.32 |

*Primary Examiner*—Anthony Green
*Attorney, Agent, or Firm*—Robert M. Downey

[57] ABSTRACT

A moisture activated, antimicrobial composition is provided which can be applied to any flexible material and in particular to woven or nonwoven textiles and disposable medical garments and masks. This composition, in a preferred embodiment, contains a quaternary ammonium compound/nonoxynol 9 complex as the pathogenic growth inhibitor.

5 Claims, No Drawings

FLEXIBLE MATERIAL HAVING BARRIER PROPERTIES

BACKGROUND OF THE INVENTION

1. Field of the Invention

The present invention relates to an antimicrobial barrier and more particularly to a moisture activated antimicrobial composition which can be applied to textiles used in the medical industry.

2. Description of the Prior Art

The prior art has contemplated many methods to afford protection to health care workers and patients against AIDS and other potentially harmful viruses and bacteria. Medical gowns and garments have been fabricated from heavyweight, non-penetrating, or waterproof materials. In recent times, however, the medical industry has demanded that the majority of articles for their use be disposable. These costly heavyweight fabrics, although potentially effective, do not lend themselves to single usage.

Some medical garment manufacturers have incorporated an antimicrobial agent within the filament or yarn structure prior to the formation of the fabric or garment. However, the effectiveness of the antimicrobial agent is not long lasting and tends to degrade or wear off prior to use.

SUMMARY OF THE INVENTION

The present invention provides a novel composition which can be applied to any flexible material and in particular to woven or nonwoven textiles either during or after manufacture to provide an antimicrobial barrier against a broad spectrum of potential pathogens. In accordance with this invention, the novel composition is moisture activated such that once applied to the fabric or material it remains inert until it comes into contact with bodily secretions, water or other liquid. A hydrophilio polymeric component of the composition breaks down and precipitates upon contact with moisture, thus activating the composition. The composition, once activated, continues to afford protection for up to 12 hours. The active antimicrobial component of the composition consists of a mixture of a quaternary ammonium compound and nonoxynol 9.

It is therefore an important object of the present invention to provide a convenient and effective means for protecting patients and medical personnel against infection.

It is a further object of the present invention to provide an antimicrobial composition which can be applied to any flexible material including but not limited to disposable medical garments and face masks, paper products, or any woven or nonwoven textile.

A further object lies in the provision of an antimicrobial composition which is moisture activated.

It is yet a further object of the present invention to provide a composition wherein the active antimicrobial component consists of nonoxynol 9 and a quaternary ammonium compound.

These and other objects will become readily apparent from the detailed description which follows.

DETAILED DESCRIPTION OF THE PREFERRED EMBODIMENTS

The present invention is directed to a moisture activated coating composition for substrates of flexible materials and in a preferred embodiment for application to disposable medical gowns, garments, and face masks. Incorporated into and throughout the composition is a functional substance which is biologically active against a broad spectrum of viruses, bacteria, fungii, and other pathogenic species. A large number of biologically active substances are available which retard bacterial, microbial, or fungal growth. It is contemplated that any of these commonly known biologically active substances could be utilized, however, in the preferred embodiment, the functional substance is comprised of a quaternary ammonium compound, nonoxynol 9, or a mixture of a quaternary ammonium compound and nonoxynol 9. The preferred quaternary ammonium compound is a blend of Myristalkonium chloride and Quaternium 14 shown by the general formula:

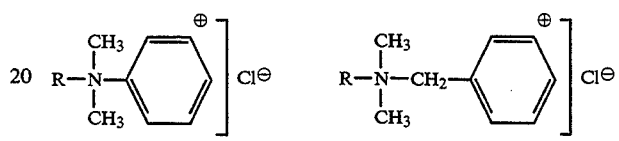

R is 60% C14, 30% C16 5% C12, 5% c18
n-alkyl dimethyl benzyl ammonium chloride and R is 68% C12, 32% c14
n-alkyl dimethyl ethylbenzyl ammonium chloride Nonoxynol 9 is an ethoxylated nonyl phenol containing 9 moles of ethylene exide and serves both as a non-ionic surfactant and an antimicrobial agent. Although both nonoxynol 9 and the blend of Myristalkonium chloride and Quaternium 14 can function alone, a synergistic effect is achieved when they are used in combination, producing substantially greater activity against pathogens than either substance alone. The nonoxynol 9 enables the coating composition to be spread evenly over the entire surface of the substrate or garment, thus achieving and maintaining a uniform antimicrobial effectiveness throughout. Nonoxynol 9 is preferably present in the amount of 1%–10% by weight and the quaternary ammonium compound blend in the amount of 0.02%–0.06% by weight.

The coating composition additionally contains a hydrophobic, waterproofing agent. The hydrophobic agent is preferably a polymer derived from vinylpyrrolidone and a long chain alpha olefin represented by the general formula:

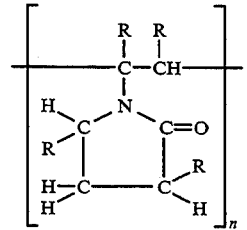

wherein R is alkyl or hydrogen

In the preferred embodiment, the hydrophobic agent is a PVP/eicosene copolymer (polyvinylpyrrolidone and eicosene) and is present 0.5%–6% by weight.

A hydrophilic film forming compound which is highly moisture sensitive and breaks down upon contact with water is further included in the coating composition. The film forming compound provides an adhesive type barrier between the functional substance and the environment, thus rendering the composition inert. Upon contact with blood or other bodily secretion, water, or any moisture or fluid in general, the hydrophilic film forming compound breaks down and precipitates, thereby allowing the functional substance to migrate to the outer surface of the substrate to effectively eliminate any pathogens present in the fluid or proximate to such. Once the film forming compound breaks down, the functional substance continues to inhibit microbial growth at the surface of the substrate or garment for up to 12 hours, thus affording protection to the wearer of the garment or any person or patient in close contact with the wearer.

Although many hydrophilic film forming agents are contemplated, preferred species include alkyl monesters or poly (methyl vinyl ether/maleic acid), represented by the following formula:

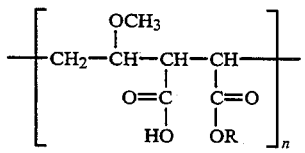

R is ethyl, isopropyl, or n-butyl Most particularly the ethyl ester of PVM/MA copolymer is selected with a molecular weight between 110,000–150,000 and present from 0.5%–6% by weight. These compounds are preferred due to their exceedingly high water sensitivity upon neutralization.

Due to the general water insoluability of the hydrophilic film forming compound, the inclusion of 2–8% by weight of an organic solvent is contemplated with anhydrous ethanol SD 40 being preferred. The organic solvent also functions as a drying agent. Anhydrous ethanol SD 40 and most other commonly utilized organic solvents exhibit relatively high flammability characteristics, therefore requiring that a stabilizer that effectively eliminates the flammable nature of the mixture be included. While the use of various stabilizers of the prior art may be acceptable to reduce flammability, 1–10% by weight of 1,3 butylene glycol is a preferred species. 1,3 butylene glycol not only effectively stabilizes the ethanol or other solvent, but further aids in dispersion.

The coating composition may also include additional materials such as aloe, present in the range of 1–5% by weight, to provide comfort to the skin and decrease the likelihood of skin irritation.

The formation of the coating composition includes the use of three separate mixing tanks. In a first mixing tank, approximately ⅓ of the total volume of the stabilizer (butylene glycol) is heated to 160 degrees F. while stirring slowly. The hydrophobic waterproof polymeric compound (PVP/eicosene) is then added and the resultant mixture is stirred until dissolved. This mixture is then cooled to 100 degrees F. In a second mixing tank, a second ⅓ portion of the butylene glycol is mixed with the functional substance (nonoxynol 9 and the quaternary ammonium compound). The hydrophilic film forming compound (PVM/MA) is then dissolved in the solvent (ethanol) in a third tank. The last ⅓ portion of the butylene glycol is then added to the third tank along with aloe and water to bring the mixture to the desired concentration. The mixture in the second tank is slowly added to the first tank under constant stirring and agitation. The mixture from the third tank is then introduced very slowly to the first tank, mixing until a homogenous mixture is achieved.

The manner of application of the resultant composition to the flexible material or garment may be varied and could include such methods as spraying, dipping, painting, or adding to the final rinse cycle during a machine washing operation. The composition will coat the material or fabric and in some instances impregnate the fiber structure of the material.

Having described the invention in detail and by reference to the preferred embodiment thereof, it will be apparent that modifications and variations are possible without departing from the appended claims.

What is claimed is:

1. An antimicrobial composition for application to a substrate comprising:
    a quaternary ammonium compound in an amount of between 0.02% to 0.06% by weight of said composition,
    an ethoxylated nonyl phenol containing 9 moles of ethylene oxide in an amount of between 1% to 10% by weight of said composition,
    1,3 butylene glycol in an amount of between 1% to 10% by weight of said composition,
    a hydrophobic waterproof polymeric compound in an amount of between 0.5% to 6% by weight of said composition,
    a hydrophilic film forming compound in an amount of between 0.5% to 6% by weight of said composition,
    an organic solvent including anhydrous ethanol in an amount of between 2% to 8% by weight of said composition,
    aloe in an amount of between 1% to 5% by weight of said composition, and
    water in an amount of between 55% to 90% by weight of said composition.

2. The antimicrobial composition as set forth in claim 1 wherein said hydrophobic waterproof polymeric compound is a copolymer of polyvinylpyrrolidone and eicosene.

3. The antimicrobial composition as set forth in claim 1 wherein said hydrophilic film forming compound is a copolymer of monoethyl ester of poly(methyl vinyl ether) and maleic acid.

4. The antimicrobial composition as set forth in claim 1 wherein said quaternary ammonium compound is a blend of n-alkyl dimethyl benzyl ammonium chloride and n-alkyl dimethyl ethylbenzyl ammonium chloride.

5. A method of producing an antimicrobial composition for application to a substrate including:
    a quaternary ammonium compound in an amount of between 0.02% to 0.06% by weight of said composition, an ethoxylated nonyl phenol containing 9 moles of ethylene oxide in an amount of between 1% to 10% by weight of said composition, 1,3 butylene glycol in an amount of between 1% to 10% by weight of said composition, a hydrophobic waterproof polymeric compound in an amount of between 0.5% to 6% by weight of said composition, a hydrophilic film forming compound in an amount of between 0.5% to 6% by weight of said composition, an organic solvent including anhydrous ethanol in an amount of between 2% to 8% by weight of said composition, aloe in an amount of between 1% to 5% by weight of said composition, and water in an amount of between 55% to 90% by weight of said composition, said method comprising the steps of:

a) heating ⅓ of a total volume of the 1,3 butylene glycol to 160 degrees F. stirring continuously,
b) adding and mixing the hydrophobic waterproof polymeric compound with the 1,3 butylene glycol in a first mixing tank to form a first mixture;
c) cooling said first mixture to 100 degrees F.;
d) mixing ⅓ of the total volume of the 1,3 butylene glycol with the quaternary ammonium compound and the ethoxylated nonyl phenol in a second mixing tank to form a second mixture;
e) mixing and dissolving the hydrophilic film forming compound in the anhydrous ethanol in a third mixing tank;
f) adding one third of the total volume of the 1,3 butylene glycol to the third mixing tank;
g) adding the water and the aloe to the third mixing tank while stirring continuously to form a third mixture;
h) gradually combining said first mixture with said second mixture in said first mixing tank; and
i) gradually adding and mixing said third mixture to said first mixing tank, stirring until a homogeneous mixture is achieved.

* * * * *